(12) United States Patent
Dubberstein et al.

(10) Patent No.: US 6,979,295 B2
(45) Date of Patent: Dec. 27, 2005

(54) AUTOMATIC COLOR GAIN ADJUSTMENTS

(75) Inventors: David Thomas Dubberstein, Waukasha, WI (US); Lihong Pan, Brookfield, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 23 days.

(21) Appl. No.: 10/717,322

(22) Filed: Nov. 19, 2003

(65) Prior Publication Data

US 2005/0107701 A1 May 19, 2005

(51) Int. Cl.$^7$ ................................. A61B 8/06
(52) U.S. Cl. ........................................ 600/455
(58) Field of Search ................. 600/437, 443, 600/447, 453–458; 367/7, 11; 73/625–626, 73/631; 382/128, 131, 162, 166–167

(56) References Cited

U.S. PATENT DOCUMENTS

| | | | |
|---|---|---|---|
| 4,926,872 A | 5/1990 | Brock-Fisher et al. | |
| 5,014,710 A | 5/1991 | Maslak et al. | |
| 5,099,848 A | 3/1992 | Parker et al. | |
| 5,161,535 A | 11/1992 | Short et al. | |
| 5,165,413 A | 11/1992 | Maslak et al. | |
| 5,190,044 A | 3/1993 | Kawasaki et al. | |
| 5,197,477 A | 3/1993 | Peterson et al. | |
| 5,257,624 A | 11/1993 | Fraser et al. | |
| 5,285,788 A | 2/1994 | Arenson et al. | |
| 5,313,948 A | 5/1994 | Murashita et al. | |
| 5,315,999 A | 5/1994 | Kinicki et al. | |
| 5,373,848 A | 12/1994 | Melton, Jr. et al. | |
| 5,409,010 A | 4/1995 | Beach et al. | |
| 5,441,052 A | 8/1995 | Miyajima | |
| 5,471,990 A * | 12/1995 | Thirsk | 600/455 |
| 5,482,045 A | 1/1996 | Rust et al. | |
| 5,505,204 A * | 4/1996 | Picot et al. | 600/507 |
| 5,579,768 A | 12/1996 | Klesenski | |
| 5,609,485 A | 3/1997 | Bergman et al. | |
| 5,622,173 A | 4/1997 | Bisson et al. | |

(Continued)

FOREIGN PATENT DOCUMENTS

| | | |
|---|---|---|
| DE | 198 19800 A1 | 12/1998 |
| EP | 0 830 842 A1 | 3/1998 |
| EP | 0 952 458 A2 | 10/1999 |

OTHER PUBLICATIONS

Joseph A. Kisslo, MD; David B. Adams, RDCS, "Doppler Color Flow Imaging #4".

(Continued)

*Primary Examiner*—Francis J. Jaworski
(74) *Attorney, Agent, or Firm*—McAndrews, Held & Malloy, Ltd.; Peter J. Vogel; Michael A. Dellapenna

(57) ABSTRACT

A system for automatically adjusting color gain of an ultrasound image. Image data passes through a wall filter and is processed into a time-gain compensation curve. Values of the time-gain compensation curve are multiplied with corresponding image data values to compensate for attenuation of image data values with increasing depth in a patient. The values used to generate the time-gain compensation curve may be averaged to reduce localized gain variations and produce an image with smoother intensity transitions. To reduce the effect of a time-gain compensation curve on overall system gain, values of the time-gain compensation curve may be scaled to produce equalized values for the time-gain compensation curve. Values of the time-gain compensation curve may be used to adjust front end gain of an ultrasound system to bring the front end gain within a few decibels of noise floor.

20 Claims, 2 Drawing Sheets

U.S. PATENT DOCUMENTS

| | | | |
|---|---|---|---|
| 5,910,119 | A | 6/1999 | Lin |
| 5,993,392 | A * | 11/1999 | Roundhill et al. .......... 600/447 |
| 6,071,242 | A | 6/2000 | Lin |
| 6,176,828 | B1 * | 1/2001 | Becker et al. .............. 600/440 |
| 6,177,923 | B1 | 1/2001 | Arenson et al. |
| 6,210,168 | B1 | 4/2001 | Aiger et al. |
| 6,267,725 | B1 * | 7/2001 | Dubberstein ................ 600/443 |
| 6,398,733 | B1 * | 6/2002 | Simopoulos et al. ....... 600/443 |
| 6,436,040 | B1 | 8/2002 | Collamore et al. |
| 6,547,736 | B1 | 4/2003 | Moehring et al. |
| 6,666,824 | B2 * | 12/2003 | Rust et al. .................. 600/443 |
| 2002/0151794 | A1 | 10/2002 | Li |
| 2003/0100833 | A1 | 5/2003 | He et al. |

OTHER PUBLICATIONS

J. Brian Fowlkes, Ph.D., "Engineering Medical Imaging Laboratory (BME 510): Ultrasound Laboratory Experiment #3," *BME 510: Winter 2003*.

Joseph A. Kisslo; MD, David B. Adams, EDCS; Graham J. Leach, MA, "Essentials of Echocardiography #1".

Eberhard Brunner, "How Ultrasound System Considerations Influence Front-End Component Choice," *Analog Dialogue 36-03 (2002)*.

Daniel W. Rickey, "Evaluation of Doppler Ultrasound Velocity and Flow Measurements".

* cited by examiner

AUTOMATIC COLOR GAIN ADJUSTMENTS

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO MATERIAL ON COMPACT DISC

Not Applicable.

BACKGROUND OF THE INVENTION

The present invention generally relates to ultrasound imaging of tissue structures. In particular, the invention relates to a method and an apparatus for improving the display of ultrasound imaging of tissue structures.

For a number of years, ultrasound imaging has been used to non-invasively monitor and image tissue structures within the human body. To produce the image, an ultrasonic transducer transmits an ultrasonic wave of energy into a patient's body. When the ultrasonic wave encounters a tissue interface, the difference in impedance between the two tissues at the interface causes an ultrasonic echo to be reflected back at the ultrasonic transducer. The time required for the ultrasonic echo to return to the ultrasonic transducer is used to determine the location where the ultrasonic echo originated. By determining where the echo originated, the location of the tissue interface causing the ultrasonic echo may be located within the patient.

As the ultrasonic wave impinges upon a tissue interface, the amplitude of the resulting ultrasonic echo depends upon the type of tissues on both sides of the interface. Some tissues will create an ultrasonic echo with a higher amplitude than other tissues. For example, an ultrasonic echo produced at a transition region from fat to muscle will generate an ultrasonic echo with a different amplitude than a transition region from a blood vessel wall to blood.

A B-mode image is an image that uses the differences in amplitude between the ultrasonic echoes to represent the tissue structure of a patient. Higher amplitude ultrasonic echoes are typically represented on the image as brighter spots and lower amplitude ultrasonic echoes are typically represented on the image as dimmer spots. By plotting the spots of varying brightness on a display, the resulting display provides an image of the transition regions between tissue structures in the patient. Because the transition regions outline the tissue structure, medical personnel are able to non-invasively see the organ and tissue structure of the patient.

Similar to a B-mode image, a color power Doppler image focuses upon the amplitude of the received ultrasonic echoes. However, unlike a B-mode image, the color power Doppler image only depicts the amplitude of ultrasonic echoes that exhibit a Doppler shift in frequency. As explained in more detail below, by only depicting the ultrasonic echoes that exhibit a Doppler shift in frequency, the color power Doppler image only depicts tissue structure that is moving inside the patient.

To produce a color power Doppler image, the ultrasonic transducer produces and transmits ultrasonic waves of energy into a patient. The ultrasonic waves travel to various depths in the body until impinging upon tissue interfaces in the body that reflect ultrasonic echoes of the ultrasonic waves back towards the transducer array.

If an ultrasonic wave impinges upon a tissue interface that is moving, the ultrasonic echo reflected back at the transducer array will contain a different frequency than the impinging ultrasonic wave. For example, if the ultrasonic wave impinges upon a tissue interface moving towards the ultrasonic transducer, the resulting ultrasonic echo will have a higher frequency than the original impinging ultrasonic wave. On the other hand, if the ultrasonic wave impinges upon a tissue interface moving away from the ultrasonic transducer, the resulting ultrasonic echo will have a lower frequency than the original impinging ultrasonic wave.

The difference between the frequency of the impinging ultrasonic wave and the resulting ultrasonic echo is referred to as a phase shift. To produce a color power Doppler image, only the amplitudes of ultrasonic echoes containing phase shifts from corresponding ultrasonic waves are displayed. Higher amplitude ultrasonic echoes are typically represented on the image as brighter spots and lower amplitude ultrasonic echoes are typically represented on the image as dimmer spots. By plotting the spots of varying brightness on a display, the resulting display provides an image of the transition regions between moving tissue structures in the patient. Consequently, medical personnel are able to non-invasively see the moving organ and tissue structure within the patient.

Similar to a color power Doppler image, a color velocity Doppler image focuses upon ultrasonic echoes that exhibit a phase shift in frequency. However, unlike a color power Doppler image, a color velocity Doppler image depicts the velocity at which tissue is moving within a patient's body.

In color velocity Doppler imaging, the level of phase shift in ultrasonic echoes is translated into a velocity value. For example, tissue moving towards the transducer array produces ultrasonic echoes with a higher frequency than the impinging ultrasonic wave. The higher the frequency of the ultrasonic echo, the higher the velocity of the movement of the tissue towards the transducer array. In contrast, tissue moving away from the transducer array produces ultrasonic echoes with a lower frequency than the impinging ultrasonic wave. The lower the frequency of the ultrasonic echo, the lower the velocity of movement of the tissue away from the transducer array.

While the intensity or amplitude of an ultrasonic echo depends on the tissue interface from which the ultrasonic echo originates, the intensity of the ultrasonic echo also depends on how deep within the patient the tissue interface is located. The deeper within the patient the tissue interface is located, the more the amplitude of the ultrasonic echo will be attenuated before it is received by the ultrasonic transducer. The more the ultrasonic echo is attenuated, the weaker the ultrasonic echo and the dimmer the spot that graphically represents the ultrasonic echo in the image. Consequently, a B-mode image and color power Doppler image gradually darken as the location on the image gets farther from the location of the ultrasonic transducer.

A conventional way to compensate for attenuation of ultrasonic echoes in ultrasound systems has been to manually adjust gain levels by rotating knobs. An operator of an ultrasound system typically selects a region of interest on a display monitor and rotates a gain knob to adjust intensity level of the displayed image to better depict the region of interest on the display. For example, if the region of interest is too dim, then the operator will increase the gain by rotating the gain knob in a positive direction. Unfortunately, increasing the gain in a region of interest to a desirable level may increase the gain in other regions on the display to undesirable levels. By increasing the gain in regions representing less attenuated data, the quantity of noise displayed in the regions representing less attenuated data may be increased. Consequently, a need exists for an ultrasound system that automatically adjusts gain level and equalizes gain level as a function of depth.

In addition, if the overall gain is too low in comparison to the noise floor, an automatic gain system that equalizes gain as a function of depth may overcompensate for the low level of overall gain. The overcompensation may produce an image with too much digital gain from the automatic gain system and not enough analog gain from a front end gain system that provides overall gain. Consequently, a need exists for a system that automatically adjusts overall gain of a front end gain system to be within a few decibels of the noise floor.

In addition, the amount of gain applied to compensate for attenuation of ultrasonic echoes and equalize gain as a function of depth may change depending on the type of wall filter used. The type of wall filter used radically effects the appearance of noise in the displayed image. Thus, the type of wall filter used will effect the noise floor. Consequently, a need exists for a system that automatically adjusts gain level, equalizes gain as a function of depth, and compensates for the type of wall filter used.

BRIEF SUMMARY OF THE INVENTION

A preferred embodiment of the present invention provides a system for automatically adjusting the gain of an ultrasonic imaging system. Ultrasonic echoes returning from structures in a patient's body include input power data, input frequency data, and depth data. The input power data is filtered by a wall filter to remove input power data associated with low frequency artifacts stemming from the movement of vessel walls.

Mean values are calculated for the input power data. The mean values of the input power data are processed into a set of time-gain compensation data for a time-gain compensation curve. An average set of time-gain compensation data may be created and used in place of the time-gain compensation data in order to reduce local gain bands in a time-gain compensation curve.

The average time-gain compensation data is used to adjust the front end gain of an ultrasound system. The maximum decibel value of the average time-gain compensation data is added to the front end gain of the ultrasound system to produce a new front end gain. The average time-gain compensation data may be recalculated with the new front end gain and the maximum decibel value added to the front end gain again. The process of calculating average time-gain compensation data and adding the maximum decibel value to the front end gain may be repeated until the front end gain is within a predetermined range of the noise floor.

After the front end gain has been adjusted to within the predetermined range of the noise floor, the average time-gain compensation data may be equalized over the depth of a region of interest to reduce the effect of the average time-gain compensation data on the overall gain. The input power data may then be multiplied by the equalized average time-gain compensation data to produce an image with the color gain automatically adjusted.

DETAILED DESCRIPTION OF THE INVENTION

Figure 1:
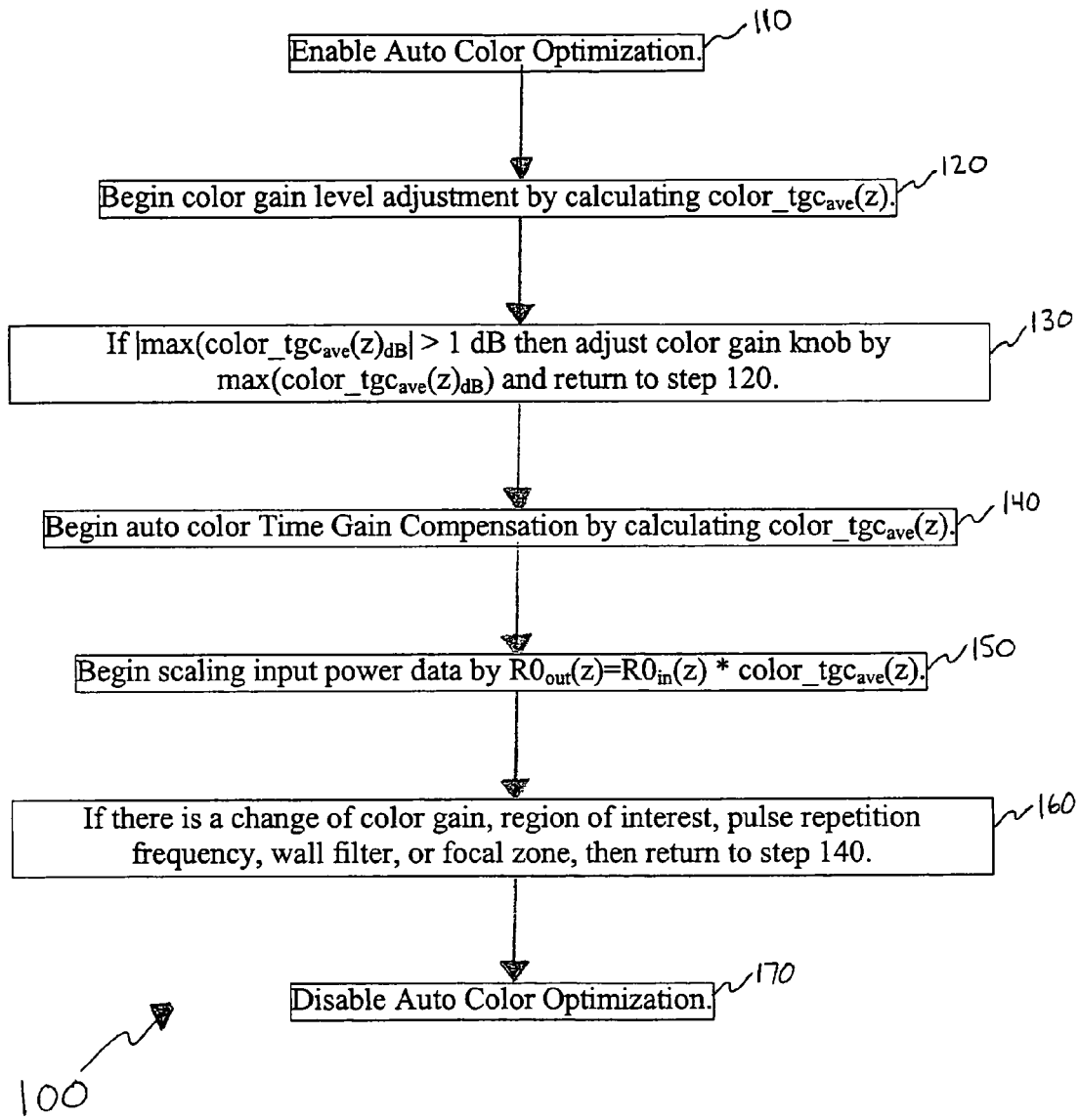
FIG. 1 shows a block diagram for a method for automatically adjusting the gain of an ultrasonic diagnostic imaging system in accordance with an embodiment of the present invention.

FIG. 1 shows a block diagram for a method for automatically adjusting the gain of an ultrasonic diagnostic imaging system 100 in accordance with an embodiment of the present invention.

In step 110, an Auto Color Optimization system is enabled. The Auto Color Optimization system is used to automatically adjust gain applied to ultrasound image data values. As a part of the Auto Color Optimization system, a color time-gain compensation curve is used.

In step 120, average values for a color time-gain compensation curve are calculated. A color time-gain compensation curve consists of compensation values that may be multiplied by image data values to compensate for attenuation of image data values as a function of depth. The color time-gain compensation curve is referred to as color_tgc(z).

To reduce local gain bands in the color time-gain compensation curve, an average of values for color_tgc(z) may be used. Average values for a color time-gain compensation curve may be represented by the equation $$\text{color\_tgc}_{ave}(z) = \frac{\sum_{z}^{z+n-1} \text{color\_tgc}(z)}{n},$$

where z is the depth within the patient and n is the number of values from the color time-gain compensation curve used to produce an average value.

Before calculating values for color_tgc$_{ave}$(z), values for color_tgc(z) must be calculated. Values for color_tgc(z) may be calculated using the equation color_tgc(z)= NF_R0/R0(z). NF_R0 is the power at a point in the processing chain which after further processing will equal a low power reject threshold. R0(z) is the power of input image data as a function of depth.

However, gain variations caused by speckle and noise add unpredictability to R0(z). Rather than use a single sample of R0(z), a mean of R0(z) may be produced to reduce variation. To produce the mean of R0(z), the data is averaged laterally at each depth of the region of interest giving a mean of R0(z) which may be referred to as <R0$_{lat}$(z)>. <R0$_{lat}$(z)> may be represented by the equation $$\langle R0_{lat}(z) \rangle = \frac{\sum_{Frame=1}^{M} \sum_{Vector=1}^{N} R0(z, \text{Frame, Vector})}{M*N}.$$

Values for <R0$_{lat}$(z)> may be calculated at every depth. For example, <R0$_{lat}$(z)> may be calculated every 200 ns (0.154 mm) with no color decimation. Consequently, to reduce gain variations R0(z) may be replaced with $<R0_{lat}(z)>$ in the calculation of the color time-gain compensation curve. With R0(z) replaced by $<R0_{lat}(z)>$, the equation for the color time-gain compensation curve becomes color_tgc(z)=NF_R0/$<R0_{lat}(z)>$.

To prevent local gain bands in the color-time gain compensation curve as a function of depth, an additional averaging may be performed in addition to the calculation of $<R0_{lat}(z)>$. Rather than average R0(z) values laterally at the same depth, the additional averaging may occur over a plurality of depths using values from the color time-gain compensation curve.

For example, a five sample moving average may be calculated with color time-gain compensation values acquired from five different depths. The additional averaging with color time-gain compensation values produces a moving average by summing the color time-gain compensation values from the sample and dividing the resulting sum by the number of values in the sample. For the case of the five sample moving average, the mathematical process for the additional range averaging may be represented by the equation $$\frac{\sum_{z}^{z+4} \text{color\_tgc}(z)}{5}.$$

Consequently, average color time-gain compensation values from the moving average may be used as an average color time-gain compensation curve represented by the equation $$\text{color\_tgc}_{ave}(z) = \frac{\sum_{z}^{z+4} \text{color\_tgc}(z)}{5}.$$

By averaging color time-gain compensation values laterally and R0(z) values vertically, local banding is reduced and an image with smoother intensity transitions is produced.

Sometimes when averaging R0(z) values laterally, the values used to calculate $<R0_{lat}(z)>$ may include values from real flow samples. If values from real flow samples are included in the calculations for $<R0_{lat}(z)>$, they may produce a dark band in an image because intensity values for real flow samples may be much greater than intensity values for noise. With intensity values much greater than noise, the values from real flow samples will increase values calculated for $<R0_{lat}(z)>$ and decrease values in the color time-gain compensation curve. Thus, the real flow samples may be excluded from the calculation of $<R0_{lat}(z)>$ to reduce the occurrence of dark bands in an image.

Exclusion of the real flow samples from the calculation of $<R0_{lat}(z)>$ may be performed with two thresholds. If variance of an R0(z) value from the other R0(z) values used in calculating $<R0_{lat}(z)>$ is less than an upper variance value, the R0(z) value is identified as a real flow sample and excluded from the calculation of $<R0_{lat}(z)>$. The upper variance value may be a scaled version of a calculated N and D variance known as varND, where $0 \leq \text{varND} \leq 1.0$. The upper variance value may be calculated with the equation upper variance=a_vari*varND$^{(power\_vari)}$, where upper variance is maxed at 1.0. A typical value for a_vari is 2.5 and power_vari is 3.0. With these values an upper variance of 0.5 or 0.7 will provide an effective method to separate non-turbulent flow from noise. Limiting the variance of R0(z) values to be less than the upper variance prevents the majority of R0(z) values representing real flow from being included in the calculation of $<R0_{lat}(z)>$.

Values of R0(z) representing turbulent flow or highly aliased flow may have a high variance. To prevent values of R0(z) representing turbulent flow or highly aliased flow with a variance greater than the upper variance from being treated as noise and included in the calculation of $<R0_{lat}(z)>$, a second threshold may be used.

The second threshold discards the R0(z) values that have a power greater than ten times the minimum power found in $<R0_{lat}(z)>$. By discarding R0(z) values that have a power greater than ten times the minimum power value found in $<R0_{lat}(z)>$, the R0(z) values representing real flow are prevented from adding too much power to $<R0_{lat}(z)>$.

In step 130, a color gain knob providing a front end gain for the ultrasound system is adjusted to bring the color system gain within a few decibels of the noise floor.

The color gain is adjusted to bring the color gain within a few decibels of the noise floor in order to optimize color in the image. Without the adjustment, if the overall gain provided by the front end gain is small, then large undesirable values for the time-gain compensation curve may be calculated. With low analog gain from the front end gain and large digital gain from the time-gain compensation curve, the color may have too much digital gain and not enough analog gain. Too much digital gain in comparison to analog gain will produce less then optimal color. If the system gain is within ten decibels of the noise floor, then the values calculated for the color time-gain compensation curve will not produce too much digital gain.

To bring the color system gain within a few decibels of the noise floor, the values calculated for color_tgc$_{ave}$(z) are converted to decibels. The average values of time-gain compensation are converted to decibels with the equation color_tgc$_{ave}$(z)$_{dB}$=10* log 10(color_tgc$_{ave}$(z)). The maximum decibel value calculated for the converted average values of time-gain compensation is added to the gain of the color gain knob that controls the front end gain. Thus, the new front end gain level supplied by the gain knob of the ultrasound system is Gain_knob=Gain_knob+max (color_tgc$_{ave}$(z)$_{dB}$). Once the front end gain has been changed, the process is repeated until the value of |max (color_tgc$_{ave}$(z)$_{dB}$)| is less than a predetermined limit, for example 1 db.

In step 140, automatic time-gain compensation of color begins by recalculating color_tgc$_{ave}$(z) after the front end gain has been adjusted per step 430. The resulting values for color_tgc$_{ave}$(z) comprise a curve of average time-gain compensation values.

If image data is multiplied by corresponding values of color_tgc$_{ave}$(z), then there may be some shift in the overall gain of the image. To minimize shift in the overall gain, the values of a time-gain compensation curve may be equalized as a function of depth.

To equalize the gain as a function of depth, the center of a region of interest is used as a pivot point around which the gain is adjusted. Equalized or scaled values of the average time-gain compensation curve may be calculated with the equation color_tgc$_{ave}$_scaled(z)=(color_tgc$_{ave}$(z)/color_tgc$_{ave}$(L/2) ), where the center of the region of interest is located at a position L/2 in a region of interest with a depth of L.

In step 150, the input power is scaled by values from color_tgc$_{ave\_}$scaled(z). The input power values R0in(z) may be multiplied by corresponding values from color_tgc$_{ave\_}$scaled(z) to output intensity values R0out(z) that are displayed on a display monitor, as represented by the equation R0out(z)=R0in(z)*color_tgc$_{ave\_}$scaled(z). R0in(z) is the input power as it enters the equalization stage and R0out(z) is the equalized output power.

In step 160, if the Auto Color Optimization system is still active, then the Auto Color Optimization system checks if the color gain changes, a new region of interest is selected, a new pulse repetition frequency is selected, a wall filter is changed, or a focal zone is changed. If the color gain changes, a new region of interest is selected, a new pulse repetition frequency is selected, a wall filter is changed, or a focal zone is changed, then the system returns to step 140.

In step 170, the Auto Color Optimization is disabled if the color gain does not change, a new region of interest is not selected, a new pulse repetition frequency is not selected, a wall filter is not changed, or a focal zone is not changed.

Figure 2:
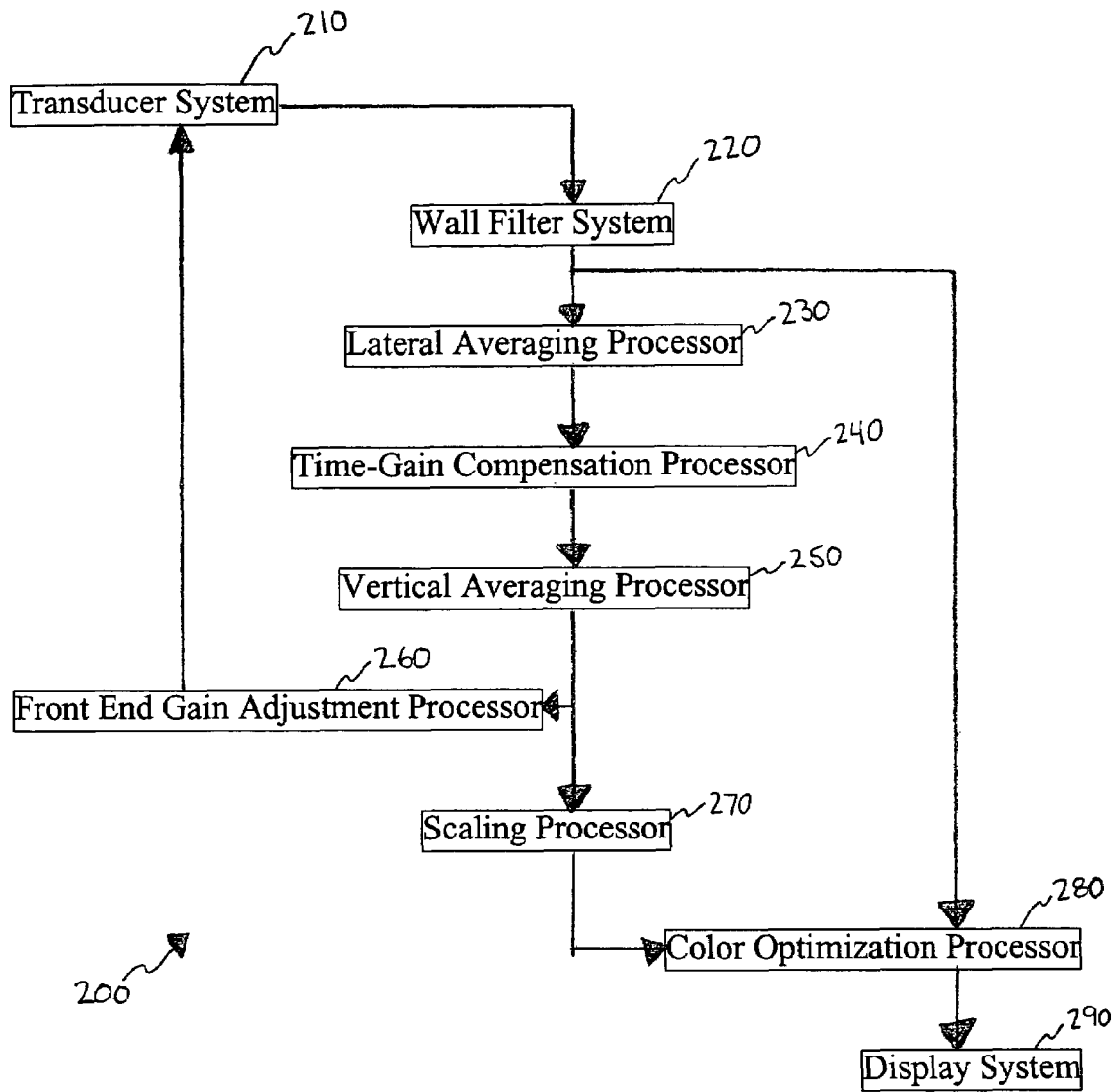
FIG. 2 shows a block diagram of an ultrasonic diagnostic imaging system in accordance with an embodiment of the present invention.

FIG. 2 shows a block diagram of an ultrasonic diagnostic imaging system 200 in accordance with an embodiment of the present invention. The ultrasonic diagnostic imaging system 200 includes a transducer system 210, a wall filter system 220, a lateral averaging processor 230, a time-gain compensation processor 240, a vertical averaging processor 250, a front end gain adjustment processor 260, a scaling processor 270, a color optimization processor 280, and a display system 290.

In operation, the transducer system 210 emits ultrasonic waves of energy into a body of a patient and receives ultrasonic echoes returning from structures within the body. The ultrasonic echoes are processed by the transducer system 210 and the transducer system 210 generates ultrasonic echo data. The ultrasonic echo data includes input power data, input frequency data, and depth data.

At least some of the ultrasonic echo data is transmitted to the wall filter system 220. The ultrasonic echo data received by the wall filter system 220 is processed by the wall filter system 220. The wall filter system 220 filters and removes ultrasonic echo data associated with low frequency artifacts stemming from the movement of vessel walls to produce filtered ultrasonic echo data. The filtered ultrasonic echo data includes filtered input power data, filtered input frequency data, and filtered depth data. The filtered input power data is transmitted to a lateral averaging processor 230.

The filtered input power data is transmitted to a lateral averaging processor 230. The lateral averaging processor 230 calculates mean values for the filtered input power data.

To calculate the mean values for the filtered input power data, the lateral averaging processor 230 selects a first input power data value from the filtered input power data. The lateral averaging processor 230 also selects at least a second input power data value from the filtered input power data, wherein the at least a second input power value represents a position in the patient located laterally in the same depth as a position in the patient represented by the first input power value.

The first input power value and said at least a second input power value are summed. The summation of the first input power value and said at least a second input power value is then divided by the number of input power values in the summation to produce a first mean input power value. A calculation of mean input power values, similar to the calculation of the first mean input power value, is repeated for all of the remaining input power data values in the filtered input power data to form a set of mean input power data.

To remove effects of real flow samples from the calculation of the set of mean input power data, the lateral averaging processor 230 may filter real flow sample data from the filtered input power data. The real flow sample data may be filtered by using power thresholds. If a variance of real flow sample data in the filtered input power data is less than an upper variance value, the real flow sample data may be removed from the filtered input power data.

Also, input power data representing turbulent flow or highly aliased flow may have a high variance. To prevent values representing turbulent flow or highly aliased flow with a variance greater than the upper variance from being included in the calculation of the time-gain compensation curve, another threshold may be used. Input power data greater than ten times a lowest power value found in the set of mean input power data may be removed from the filtered input power data.

The mean input power data is transmitted from the lateral averaging processor 230 to the time-gain compensation processor 240. The time-gain compensation processor 240 calculates a set of time-gain compensation data for a time-gain compensation curve. The set of time-gain compensation data is created by individually dividing a low power reject threshold by each of the values in the set of mean input power data. The set of time-gain compensation data is transmitted from the time-gain compensation processor 240 to the vertical averaging processor 250.

The vertical averaging processor 250 calculates a set of average time-gain compensation data from the set of time-gain compensation data received from the time-gain compensation processor 240. To calculate a set of average time-gain compensation data from the set of time-gain compensation data, the vertical averaging processor 250 selects a first time-gain compensation data value from the set of time-gain compensation data. The vertical averaging processor 250 then selects at least a second time-gain compensation data value from the set of time-gain compensation data. Said at least a second time-gain compensation data value represents a position in the patient located directly vertical above or below a position in the patient represented by the first time-gain compensation data value.

The first time-gain compensation data value and said at least a second time-gain compensation data value are summed. The summation of the first time-gain compensation data value and said at least a second time-gain compensation data value is then divided by the number of time-gain compensation data values in the summation to produce a first average time-gain compensation data value. A calculation of average time-gain compensation data values, similar to calculation of the first average time-gain compensation data value, is repeated for all of the remaining time-gain compensation data values in the set of time-gain compensation data to form a set of average time-gain compensation data. The vertical averaging processor 250 transmits the set of average time-gain compensation data to a front end gain adjustment processor 260.

The front end gain adjustment processor 260 adjusts the color gain of the ultrasound diagnostic imaging system 200 within a few decibels of a noise floor. The average time-gain compensation data values in the set of average time-gain compensation data are converted to decibel average time-gain compensation data values by multiplying the logarithm of the average time-gain compensation data values by ten. A maximum decibel value in the decibel average time-gain compensation data values is transmitted to the transducer 210. The transducer system 210 adds the maximum decibel value to front end gain of the transducer system 210. The front end gain adjustment processor 260 continues to calculate the maximum decibel value using average time-gain compensation data supplied by the vertical averaging processor 250 until the system color gain is within a few decibels of the noise floor.

The vertical averaging processor 250 transmits the set of average time-gain compensation data to the scaling processor 270. The scaling processor 270 equalizes the values in the set of average time-gain compensation data to produce a scaled set of average time-gain compensation data. To produce the scaled set of average time-gain compensation data, the scaling processor 270 divides all of the values in the set of average time-gain compensation data by a scaling value in the set of average time-gain compensation data. The scaling value may be any value in the set of average time-gain compensation data. Preferably, the scaling value represents a position in the patient located halfway between the top of a region of interest and the bottom of a region of interest.

The scaling processor 270 transmits the scaled set of average time-gain compensation data to the color optimization processor 280. The color optimization processor 280 produces color optimized data by multiplying the filtered input power data from wall filter system 220 by corresponding values from the scaled set of average time-gain compensation data from the scaling processor 270. The color optimized data is transmitted from the color optimization processor 280 to the display system 290. The display system 290 displays an image of the color optimized data.

In the alternative, the lateral averaging processor 230, the time-gain compensation processor 240, the vertical averaging processor 250, the front end gain adjustment processor 260, the scaling processor 270, and the color optimization processor 280 may be combined into fewer processors. For example, the lateral averaging processor 230, the time-gain compensation processor 240, and the vertical averaging processor 250 may be combined into a single processor that produces a set of average time-gain compensation data from input power data. As another example, the lateral averaging processor 230, the time-gain compensation processor 240, the vertical averaging processor 250, the front end gain adjustment processor 260, the scaling processor 270, and the color optimization processor 280 may be combined into a single auto color optimization processor.

What is claimed is:

1. A method for automatically adjusting color gain of an ultrasound imaging system comprising:
   filtering input power data with a wall filter to produce filtered input power data; and
   processing said filtered input power data to produce a set of time-gain compensation data.

2. The method of claim 1 further comprising:
   averaging time-gain compensation data values in said set of time-gain compensation data to produce a set of average time-gain compensation data.

3. The method of claim 2 further comprising:
   converting values of average time-gain compensation data in said set of average time-gain compensation data to decibel average time-gain compensation values, wherein said decibel average time-gain compensation data values are in decibel format;
   selecting a maximum value from said decibel average time-gain compensation data values; and
   adjusting front-end gain of said ultrasound imaging system by adding said maximum value to said front-end gain.

4. The method of claim 3 wherein said front-end gain is adjusted to within a few decibels of a noise floor.

5. The method of claim 2 further comprising:
   scaling said set of average time-gain compensation data to produce a scaled set of average time-gain compensation data.

6. The method of claim 5 wherein said scaling step comprises:
   selecting a scaling value from said set of average time-gain compensation data; and
   dividing said set of average time-gain compensation data by said scaling value.

7. The method of claim 5 further comprising:
   equalizing said filtered input data by multiplying said filtered input data by a corresponding value from said scaled set of average time-gain compensation data.

8. The method of claim 2 wherein said averaging step includes averaging values of filtered input power data laterally to produce a set of mean input power data.

9. The method of claim 2 wherein said averaging step includes averaging values from said set of time-gain compensation data vertically.

10. The method of claim 1 wherein said set of time-gain compensation data may be used to compensate for attenuation of said filtered input power data as a function of depth within a patient.

11. An ultrasound imaging system including:
    a wall filter for filtering input power data to produce filtered input power data;
    a lateral averaging processor for processing said filtered input power data into a set of mean input power data; and
    a time-gain compensation processor for processing said set of mean input power data into a set of time-gain compensation data.

12. The system of claim 11 further including:
    a vertical averaging processor for averaging time-gain compensation data values in said set of time-gain compensation data to produce a set of average time-gain compensation data.

13. The system of claim 12 further including:
    a front end gain adjustment processor for converting values of average time-gain compensation data in said set of average time-gain compensation data to decibel average time-gain compensation data values,
    wherein said decibel average time-gain compensation data values are in decibel format.

14. The system of claim 13 wherein said front end gain adjustment processor determines a maximum value in said decibel average time-gain compensation data values and adjusts front-end gain of said ultrasound imaging system by adding said maximum value to said front-end gain.

15. The system of claim 14 wherein said front-end gain is adjusted to within a few decibels of a noise floor.

16. The system of claim 12 further including:
    a scaling processor for scaling said set of average time-gain compensation data to produce a scaled set of average time-gain compensation data.

17. The system of claim 16 wherein said scaling processor determines a scaling value in said set of average time-gain compensation data and divides said set of average time-gain compensation data by said scaling value.

18. The system of claim 17 including a color optimization processor for equalizing said filtered input power data by multiplying said filtered input power data by a corresponding value from said scaled set of average time-gain compensation data.

19. The system of claim 12 wherein said vertical averaging processor vertically averages values from said set of time-gain compensation data.

20. The system of claim 11 wherein said lateral averaging processor laterally averages values in said filtered input power data.

* * * * *